United States Patent [19]
Cosman

[11] 4,206,762
[45] Jun. 10, 1980

[54] TELEMETRIC DIFFERENTIAL PRESSURE SENSING METHOD

[76] Inventor: Eric R. Cosman, 872 Concord Ave., Belmont, Mass. 02178

[21] Appl. No.: 895,956

[22] Filed: Apr. 13, 1978

Related U.S. Application Data

[62] Division of Ser. No. 697,948, Jun. 21, 1976, abandoned.

[51] Int. Cl.² ............................................. A61B 5/00
[52] U.S. Cl. ........................................ 128/660; 73/701; 73/717; 73/718; 128/675; 128/748
[58] Field of Search ............... 128/675, 660, 673, 748; 73/701, 708, 716–719, 722

[56] References Cited

U.S. PATENT DOCUMENTS

| | | | |
|---|---|---|---|
| 3,034,356 | 5/1962 | Bieganski et al. | 128/748 |
| 3,038,465 | 6/1962 | Allaro et al. | 128/675 |
| 3,720,108 | 3/1973 | Freitag | 73/722 |
| 3,722,373 | 3/1973 | Beach et al. | 73/716 X |
| 3,724,275 | 4/1973 | Battaglini et al. | 73/716 |
| 3,727,463 | 4/1973 | Intraub | 73/398 R |
| 3,757,770 | 9/1973 | Brayshaw et al. | 128/748 X |
| 3,853,117 | 12/1974 | Murr | 128/748 X |
| 3,859,484 | 1/1975 | Nelson | 73/716 X |
| 3,943,915 | 3/1976 | Severson | 73/406 X |
| 4,014,319 | 3/1977 | Favre | 128/748 |
| 4,026,276 | 5/1977 | Chubbuck | 128/653 |
| 4,067,241 | 1/1978 | Corbett | 73/717 |
| 4,141,348 | 2/1979 | Hittman | 128/748 |

OTHER PUBLICATIONS

Collins, C. C., *IEEE Trans. On Bio.–Med. Engng.* vol. 14, No. 2, Apr. 1967, pp. 74–83.
Atkinson, J. R. et al., *Journ. of Neurosurgery,* 1967, vol. 27, No. 5, pp. 428–432.

*Primary Examiner*—Kyle L. Howell
*Attorney, Agent, or Firm*—Richard J. Birch

[57] ABSTRACT

A differential pressure sensing device is fully implanted in the body of a patient to monitor internal pressure such as intracranial pressure. A movable element in the sensor communicates with the internal pressure of the body to be measured on one side and the atmospheric pressure on the other, the latter communicated through the intact skin and a nearly coplanar membrane. The movable element's differential pressure dependent displacement changes a physical characteristic of the sensor, such as the resonant frequency of a tuned L-C circuit, and the change is detected external to the body by a radiating detector system, such as a frequency swept radio frequency oscillator, by which the internal pressure is read out.

18 Claims, 14 Drawing Figures

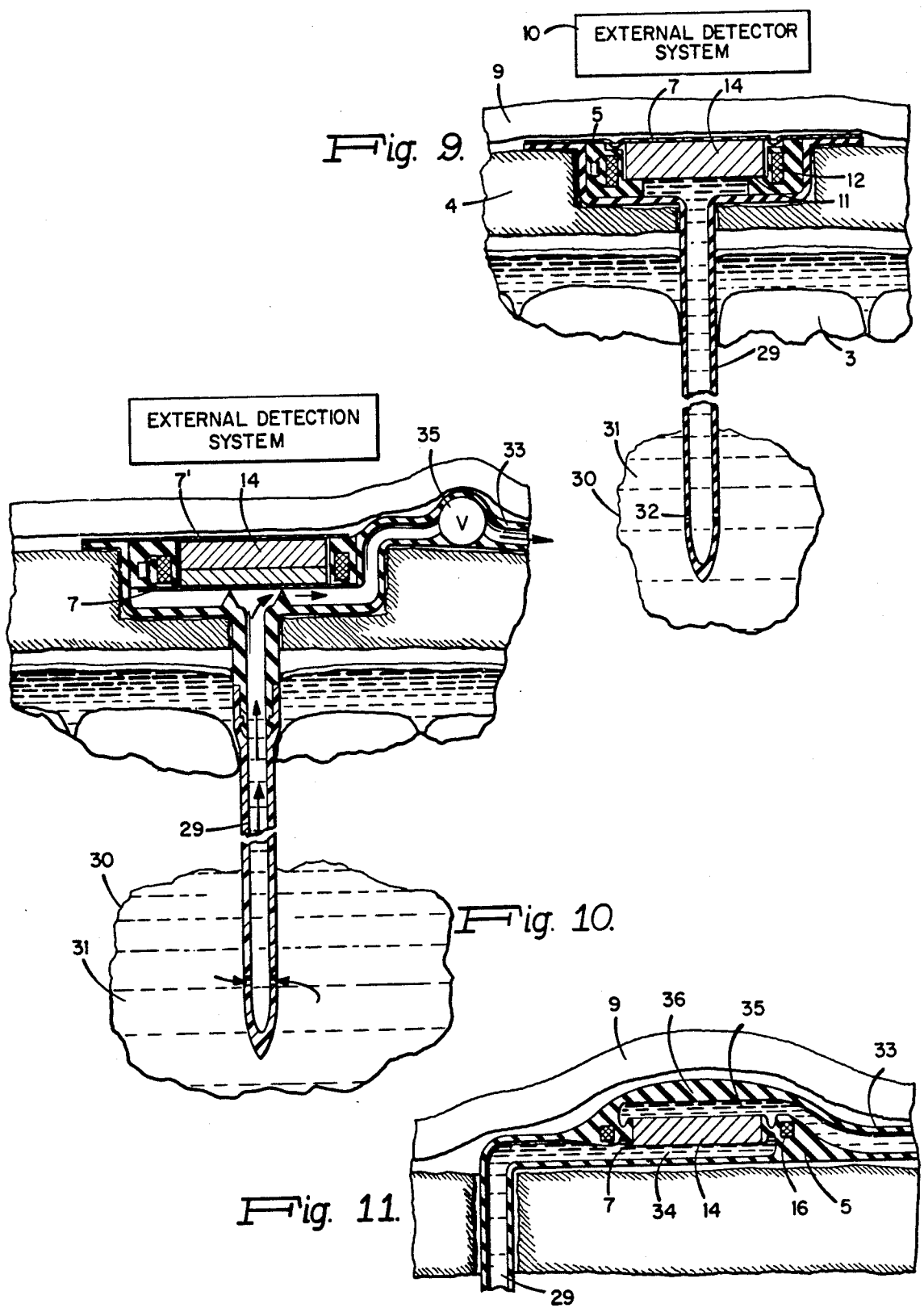

TELEMETRIC DIFFERENTIAL PRESSURE SENSING METHOD

CROSS REFERENCE TO RELATED APPLICATION

This application is a divisional application of Ser. No. 697,948, filed June 21, 1976, now abandoned, by Eric R. Cosman for A Telemetric Differential Pressure Sensing System and Method Therefore.

BACKGROUND OF THE INVENTION

The invention relates to the precision measuring and monitoring of pressures in the living body, such as intracranial pressure in the head, by means of a long-term, totally implanted sensor which undergoes a conformational change with pressure and which is coupled through the skin by electromagnetic, acoustic, or mechanical transmission to an external device which detects that change and interprets the pressure. The invention refers additionally to a device which is automatically barometric compensated, has immediate zero point reference check, can be made passive, and is insensitive to barometric or temperature changes.

At the present time there is no such wireless device available for general clinical or research purposes. The uses for such a device in neurosurgery would be immediate in the management of intracranial hypertension, monitoring of intracranial pressure in all cases of intracranial neurosurgery and head trauma, longterm diagnostics for evidence of tumor recurrence, and management of hydrocephalus.

All devices previously proposed have significant shortcomings which make them impractical for widespread, safe, accurate, reliable, and long-term use as intracranial pressure monitors. Most designs involve a tube or wire connection through the skin to an external device, and since this greatly increases the chance of infection and electrical shock to the patient and reduces the patient's mobility they are hazardous and impractical. Of the devices which are wireless and fully implanted, they usually involve a sealed inner volume containing a fixed amount of gas, this being housed in a flexible container which deflects under pressure. The major problems with this design aspect are the following: liquids and gases will inevitably diffuse through the membranes and walls of the container causing steady drift of the zero-point reading, and causing an unpredictable error in the device's calibration; changes in barometric pressure will cause significant variations in the body pressure relative to the fixed volume pressure and thus the device's pressure readout must be corrected for barometric pressure changes in the external detection system; a trapped volume of significant size could make it dangerous for a patient to experience atmospheric pressure change, such as those found in air travel, for fear of rupturing the device; and temperature changes in the patient will cause changes in the trapped volume and resultant errors in the pressure reading. Previous totally implanted designs provide no means to check out their zero-pressure calibration after implantation and thus no means to determine diffusion or temperature drifts in the readings nor any check of the proper function of the device, which is essential for long and short-term implantation. Most previous designs are of complex construction, involve high tolerance parts and assembly, and are not amenable to calibration standardization; all of which make them expensive, inaccurate, and unsuitable for simple and general application.

Accordingly, some of the principal objects of the present invention are the following:

(1) To provide a pressure detector which can be implanted for an indefinite period under a fully intact skin with no wire or tube connections to the exterior so as to reduce infection and electrical shock hazard, and to read pressures in inaccessible spaces in the body, such as intracranial pressure, with an accuracy of 5 to 10% or better.

(2) To eliminate or make insignificant all inaccuracies, and dependencies on a trapped volume of gas or fluid in the device, to make the pressure readings insensitive to drifts from membrane permeability, barometric change, and temperature variation, and to eliminate the hazard of rupturing the device during air travel.

(3) To provide automatic barometric compensation as a built-in feature of the implanted device.

(4) To provide a means of easily and instantly checking the zero-pressure calibration of the device.

(5) To provide a sufficiently fast dynamic response to enable observation of variations in the body pressure due to heart rate, respiration, and any other physiological changes.

(6) To allow a simple calibration standardization of the implant.

(7) To allow the implanted device to be of simple, passive, compact, and low cost construction so as to be implanted permanently and to function properly for indefinitely long periods.

(8) To make the system amenable to telemetry over long distances so as to monitor pressures in a freely moving patient.

SUMMARY OF THE INVENTION

The above objects and advantages are achieved by the present invention as described in the following brief summary: The implanted pressure sensor comprises an insulating body with a movable element that moves through an opening or channel in the body. The movable element communicates with external atmospheric pressure on one side by means of a membrane which is nearly coplanar with the intact skin covering it, and with the internal pressure on the other side, also by a membrane, so that the degree of the movable element's displacement relative to the body is directly related to the difference in the internal and atmospheric pressures. Thus, since the pressure-dependent distortion of the implanted sensor does not involve variation of the volume of a trapped gas or space all problems related to the latter are eliminated. Also, since direct sensing of atmospheric pressure is exploited, barometric compensation is built-in and automatic. Further, the skin may be pressed manually just above the implanted device, and the movable element can be thus pushed back to a stop point in the device's body corresponding to equilibirium; thereby allowing the zero-point pressure position to be checked instantly at any time. The implanted device is coupled to an external detection system by electromagnetic, acoustic, or other radiation or transmission means across the intact intervening skin. The external detector system can determine the position of the movable element's displacement and thus the difference between the internal and atmospheric pressures. A variety of means of interrogating the implant by the external device are possible, but a particularly simple method involving a passive implant consists of building a fixed and parallel coil and capacitor combination into the body of the implant and a magnetic material into the movable element which moves through the coil, thus varying its inductance with varying displacement or internal pressure. The internal L-C resonant circuit is coupled electromagnetically to an external swept oscillator pickup circuit which detects the resonant frequency of the L-C circuit and related it to the coils plus magnetic material's inductance and corresponding internal pressure. As will be shown below, this construction is simple, compact, economical, free of thermal, diffusion, or mechanical drifts, calibration standardized, fast responding, adaptable to remote telemetry, and incorporate in a large number of multiple function implant configurations.

A fuller understanding of the invention and additional objects, advantages, and novel aspects of its will be gained from the following detailed description, illustrative drawings, and various embodiments and implementations. There are many design variations on the present invention concept which are possible, such as, constructional details, choice of specific conformations, various methods of coupling and information transfer from implant to external detector, and variations on the electronic design within the state of current electrical engineering art of both implanted and external circuitry. Such variations which are included within the scope of the claims below are understood to be included in the present invention disclosure. Furthermore, although the present inventive concept may be adapted to pressure measurement in numerous locations in the human body, it is highly illustrative to show its application as an intracranial pressure monitor. It is understood that the scope of the invention covers the use in areas of the body other than just the head.

DESCRIPTION OF THE DRAWINGS

In the following drawings similar reference characters represent similar parts.

FIG. 9 shows a view in vertical section of another more compact variation of the concepts of FIGS. 1 and 2 utilizing a single membrane and being incorporated in a system for measuring intraventricular pressure.

FIG. 10 shows a design similar to that in FIG. 9 but working in conjunction with a cerebrospinal fluid shunt valve.

FIG. 11 illustrates differential sensor of pressures in two different regions.

Referring to FIG. 1, the major elements of the implanted pressure sensor, used in this example as a monitor of epidermal intracranial pressure if the dural membrane 1 is intact or of cerebrospinal fluid 2 pressure that surrounds the brain 3 if the dura 1 is cut, may be understood as follows: The sensor, which is inserted in a burr hole drilled in the skull 4 comprises a housing 5 having a through opening in which travels a movable element 6. An inner flexible diaphragm 7 attached to housing 5 communicates the intracranial pressure P(ICP) to one side of movable element 6 while an outer diaphragm 7' communicates the pressure of the atmosphere 8, P(ATM) which is transmitted across the intact scalp 9, to the other side of 6. By this system a difference in P(ICP)−P(ATM) will cause a force imbalance on the inner diaphragm 7, and by properly spring loading the movable element 6 relative to the housing 5 a calibrated relationship of the displacement of the movable element relative to the housing can be achieved.

This displacement will cause calibrated physical or electrical changes in some characteristic or parameter within the sensor, and these changes are detected by an external detection system 10 which is coupled to the sensor by electromagnetic, acoustic, or other means across the skin, but not through the skin as by a tube or wire. The detector 10 thus interpretes the displacement and reads out the associated barometrically compensated intracranical pressure P(ICP)−P(ATM). A mechanical stop, fiducial, or shoulder 11 is employed to interrupt the downward movement of the movable element relative to the housing so that by pressing on the skin just above diaphragm 7' an instant check of the zero-point of P(ICP)−P(ATM) can be made.

Figure 1:
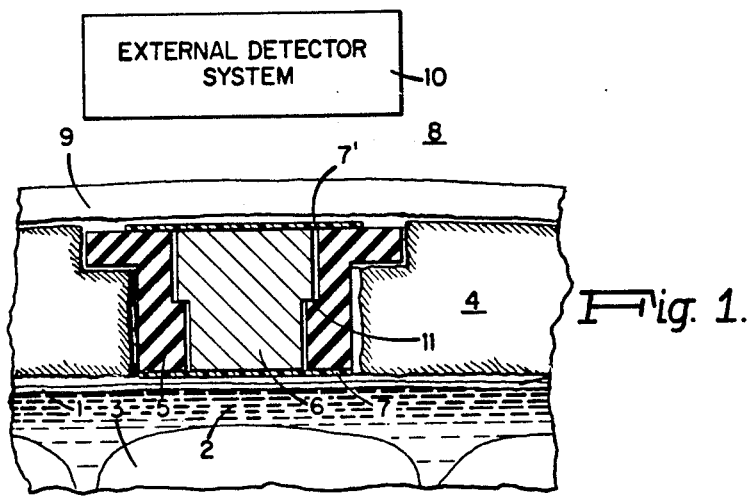
FIG. 1 shows a schematic, vertical sectional view of an implanted sensor being used to measure intracranial pressure in a living human being.
Figure 2:
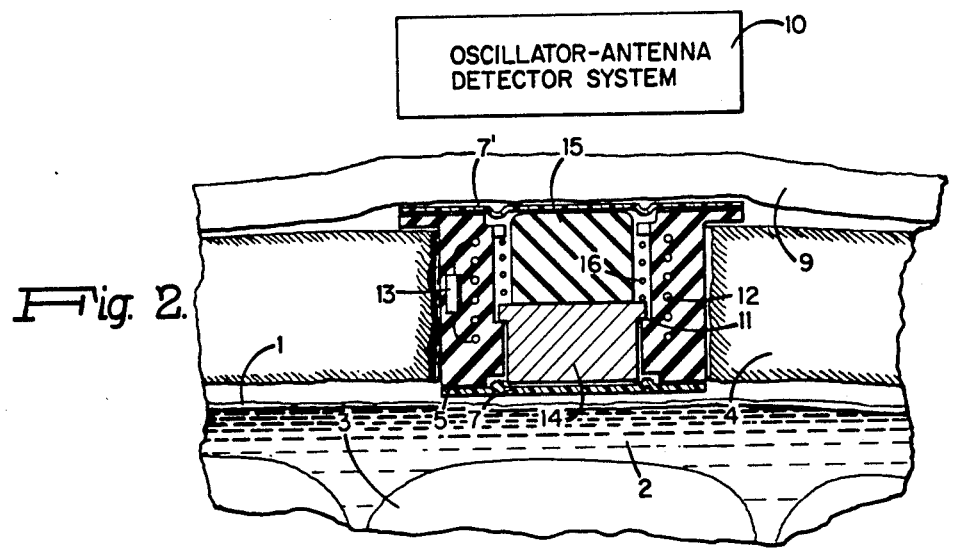
FIG. 2 shows a view in vertical section of a more specific design of the invention concept of FIG. 1 for intracranial pressure measurement.

Referring to FIG. 2, a specific and practical design involving the basic inventive concepts of FIG. 1 is shown. The cylindrical housing 5 is formed of an insulating plastic, such as, nylon or "Lexan", and has an upper flange so that it seats in a standard burr hole in the skull 4. A fixed coil 12 and capacitor 13 are imbedded in the housing to form a parallel L-C tank circuit. A slug 14 of magnetic material moves in a cylindrical hole through the housing 5 and is attached to coaxial cylindrical member 15, made of a plastic material, to form the movable element 6 of FIG. 1. The two diaphragms 7 and 7' are made of thin plastic material, preferably convoluted for flexibility, and hermetically attached to housing 5. The diaphragms contact the ends of slug 14 and cylindrical member 15, respectively. The two diaphragms 7 and 7' in combination with the slug 14 and member 15 form a dual motion-coupled diaphragm system with end-for-end symmetry such that P(ICP) is felt on one end, P(ATM) is communicated through the intact skin and is felt on the other end, and the external force on the slug 14 and member 15 is directly proportional to the difference $\Delta P = P(ICP) - P(ATM)$.

When P(ICP) is greater than P(ATM), the magnetic slug 14 will move upward relative to coil 12 thus changing the inductance of the coil-magnetic slug system. This in turn will cause a change in the resonant frequency of the L-C tank circuit, which is detected outside the body by an external detector system 10 described below. The magnetic slug 14 moves against a spring 16 so that the amount of its displacement X is proportional to the pressure imbalance $\Delta P$; i.e. $\Delta P = P(ICP) - P(ATM) = kx$, where k is the spring constant. Thus the change in resonant frequency of the L-C circuit can be directly related to $\Delta P$.

Figure 3:
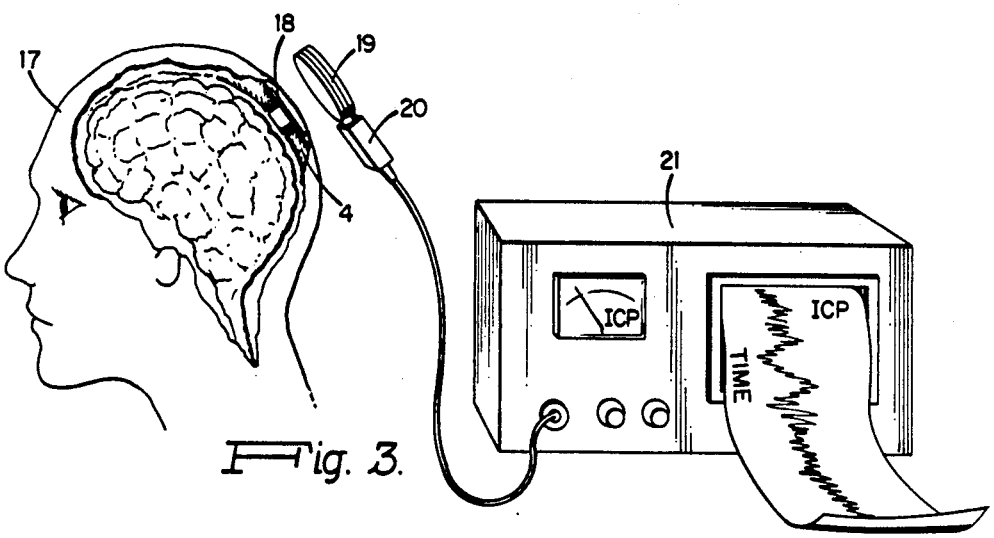
FIG. 3 illustrates the arrangement of the sensor such as that in FIG. 1 relative to the external "grid-dip" type oscillator with pickup antenna and the other associated circuitry for signal analysis and digital or chart recorder readout of the intracranial pressure.

Detection of the sensor's L-C resonant frequency, and thus the atmospherically compensated intracranial pressure can be easily accomplished by coupling the sensor's L-C circuit electromagnetically to the external antenna-oscillator system 10 which can detect a power dip at the resonant L-C frequency. Such detector circuits have been well known in radio engineering for decades as "grid-dip" oscillators and now can be made very compactly with integrated circuits. Such dip oscillators operate typically at 10 to 100 Mega Hertz and are swept over the resonant frequency at audio rates. The resonant power dip signal is detected by common peak detection methods. FIG. 3 illustrates a typical arrangement of patient 17, sensor 18, and external detection system. The external pickup antenna 19 can be coupled satisfactorily at several inches from the patient's head and forms the inductance of the swept oscillator contained in box 20. The frequency dip signal of the oscillator is analyzed in console 21 and displayed by analog or digital meters or by chart recorder.

Several ancillary points and advantages of the design in FIG. 2 enable the aforestated objects of the invention to be achieved. The end-for-end symmetry of the dual motion-coupled diaphragm system, plus the convoluted flexible diaphragms, plus the very small innerspace V(IN) which is required only for wall clearance of the spring and the cylinders 14 and 15 not only make automatic barometric compensation possible, but also eliminate drift due to diaphragm permeability, aberrations due to barometric pressure change, and hazard of rupture during air travel. If the innerspace volume V(IN) is initially filled with air and if diffusion of this gas outward and of fluid inward after implantation cause a reduced pressure P(IN) in V(IN), then because of end-for-end symmetry of 7, 7', 14, and 15 the forces on diaphragms 7 and 7' will be the same function of P(ICP)−P(IN) and P(ATM)−P(IN), and thus the net force, and associated displacement, of cylinders 14 and 15 will depend only on $\Delta P = P(ICP) - P(ATM)$ and not on P(IN). Should a sudden change of $\delta P(ATM)$ in barometric pressure, P(ATM), occur as in air flight the change in V(IN) will be roughly $$\delta V(IN) \approx -\frac{\delta P(ATM)}{P(ATM)} V(IN)$$

and if V(IN) is very small, so will be $\delta V(IN)$. Thus, the perturbation on and danger of rupturing of diaphragms 7 and 7' will be accordingly small, and again end-for-end symmetry will cancel any effect on the measurement of $\Delta P$. The same argument applies to changes in P(IN) or V(IN) because of changes in surrounding temperature.

The novel features of the external communication of the sensor through the skin and the provision of a shoulder stop 11 for elements 14 and 15 against the housing 5 at equilibrium position, not only allow an instant zero pressure reference check, but also insures an instant check of the operation of the entire system and correction to any temperature dependent variations in the electro-mechanical characteristics of the sensor. The coil 12 the capacitor 13 can easily be selected for negligible temperature drift and high resonant Q. The cylindrical elements 14 and 15 can be teflon coated and axially suspended on diaphragms 7 and 7' so that friction is minimized and the static and dynamic response and sensitivity are maximized.

The design has been demonstrated in implantations to detect differences in intracranial pressure of less than 5 mm of $H_2O$ and to record easily the rapid pressure variations due to heart beat and respiration, these being important clinical indications of a working system which previous designs cannot achieve. The diaphragms 7 and 7' may be arranged coplanar with the dura 1 and scalp 9, respectively, during equilibrium so that surface tension effects of the latter are minimized and fibrosis of the dura will not occur in long implantations, a problem which has plagued previous designs. The sensor is cosmetically inobtrusive, lying flat with the scull 4, and a full range of clinically important pressures from 0–100 cm of water may be read with only ½ mm total displacement of cylinder 14 and 15. The design of FIG. 2 can be made less than ½ inch in diameter and as shallow as 3 to 11 mm total height, making them adaptable to infants or small animals as well as adults. The design is easily calibration standardized by selection of construction materials and springs of accurate spring constant k. The design is intrinsically simple for high volume, low manufacture. It can be made of biocompatible material and covered with a thin silicone rubber enclosure.

It is understood that many variations of the basic concepts disclosed in FIGS. 1, 2 and 3 are possible and included in this disclosure. The sensor may have only one diaphragm, which feels P(ICP) on one side and P(ATM) on the other. The movable element, equivalent to 6 in FIG. 1, may be attached to the single diaphragm of the displacement of it and the diaphragm is detected externally. In the dual motion-coupled diaphragm design, the diaphragms 7 and 7' may not be stacked as in FIG. 1, but located at more remote separation. The coupling element 6 may be a rigid mechanical means such as a cylinder or linkage, or may be a fluid transmitted through the body by a tube or channel. The physical characteristic of the sensor which is changed and detected with change of differential pressure $\Delta P = P(ICP) - P(ATM)$ may be diverse, and accordingly, so may be the detection means. For example, referring to FIG. 1, the body 5 and movable element 6 may be scatterers or absorbers of mechanical, acoustic, or ultrasonic waves or of electromagnetic waves such as micro waves or infrared radiation and the external detection system 10 may involve a source, interferometer, echo detector, frequency or amplitude detector of these waves by which the configuration or displacement of 6 relative to 5 may be determined. Unlike the design of FIG. 2, the sensor may contain active circuits with stored energy cells or induction power circuits. Many variations of the passive L-C circuit system of FIGS. 2 and 3 are possible, involving other kinds of variable inductors, variable capacitors, both variable inductors and capacitors, or variable resistors to change the resonant frequency or impedance with pressure. Wide latitude is possible in choice of geometry, size, configuration of components, coil and ferrite geometries, and frequency of the design of FIG. 2. The magnetic slug may be replaced by a conductive metal slug to achieve induction change by eddy current detuning. The coil spring 16 may be replaced by a leaf, lever, or strap springs affixed to the body 5 at one end and to the movable cylinder 14 plus 15 in FIG. 2 or 6 in FIG. 1. The diaphragm or diaphragms may be convoluted as a speaker or rolling diaphragm or as a usual cylindrical bellows to achieve flexibility. The diaphragm may be metal or metal-coated or made of a variety of strong, impermeable, and flexible materials. Initially, the inner spaces of the sensor may or may not contain fluid. If fluid is used to fill the inner spaces or to act as diaphragm coupling, a simple way of insuring that its amount will remain constant is to make it a water solution of the same ionic concentration as the cerebrospinal fluid and intracellular fluid. In this way, the osmotic pressures are equal inside and outside the sensor and the net diffusion flow across the diaphragms will be zero.

Figure 4:
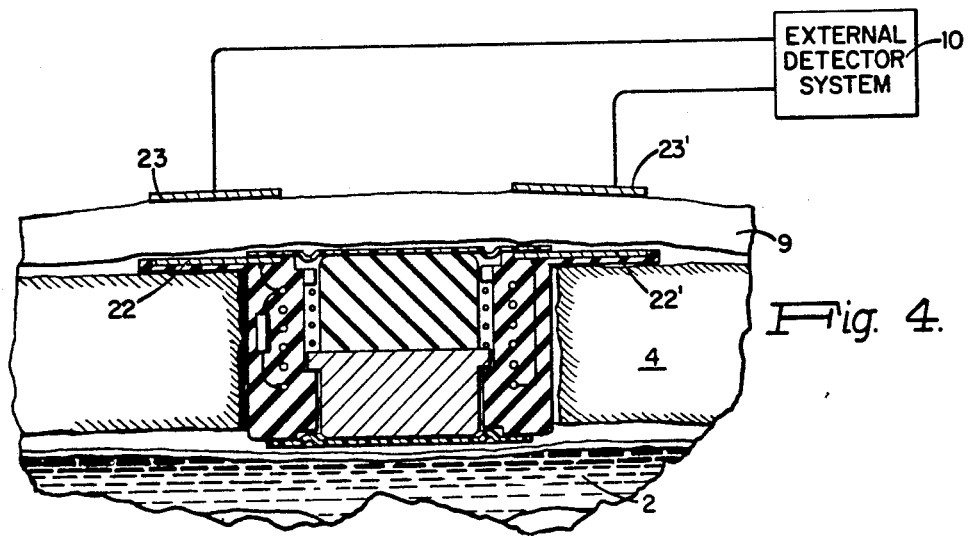
FIG. 4 shows another variant of the design of FIG. 2 in which a capacitive type electronic coupling through the skin is used to determine the resonant frequency of the internal L-C circuit.
Figure 5:
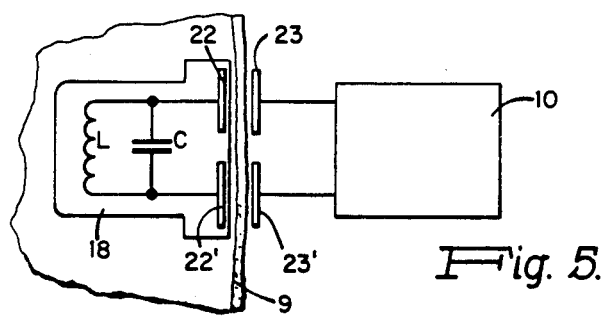
FIG. 5 is a schematic circuit and block diagram illustrating the method used in FIG. 4.

Other specific embodiments of the invention concept of FIG. 1 are possible in which substantively different external coupling means from that of FIG. 2 are used. FIGS. 4 and 5 illustrate an example of a sensor which incorporates an L-C resonant circuit similar to that in FIG. 2 but different method of electromagnetic coupling across the skin 9 to the external detector system 10. The coupling method is transcutaneous capacitive coupling and is done by area electrodes 22 and 22' near the upper surface of the sensor. These are in proximity to electrodes 23 and 23', respectively, on the skin. At the L-C resonant frequency the capacitive reactive of these pairs of adjacent electrodes is small, and thus one can use the resonant frequency of the implanted L-C circuit to determine the frequency of oscillation of an external strongly coupled oscillator housed in 10 which can then be measured by the analyzer-readout console. This type of sensor coupling has several important advantages. First it allows a nearby stable and fixed coupling, and circumvents the possible problems of holding pickup coil 19 of FIG. 3 near the sensor 18. In addition, it would allow for a compact transmittor system in 10 so that the intracranial pressure information may be telemetered to a remote monitoring console, while the compact battery operated oscillator is carried along with the patient or animal under examination. Thus the design of FIGS. 4 and 5 represents a unique system with all the advantages of the concepts of FIGS. 1, 2 and 3 as well as the capability of performing intracranial pressure studies and monitoring a great variety of subject activities.

It is understood that variants of the transcutaneous coupling scheme of FIGS. 4 and 5 are assumed in this disclosure. For example, whereas in FIGS. 4 and 5 an inductor L and capacitor C are built into the sensor, either one of which or both of which may vary with pressure, it is also possible that only the pressure sensing inductor L, or capacitor C, may be in the implanted sensor, and that the other element of the L-C circuit, C or L respectively, may be in the external system 10 along with the strongly coupled oscillator.

Figure 6:
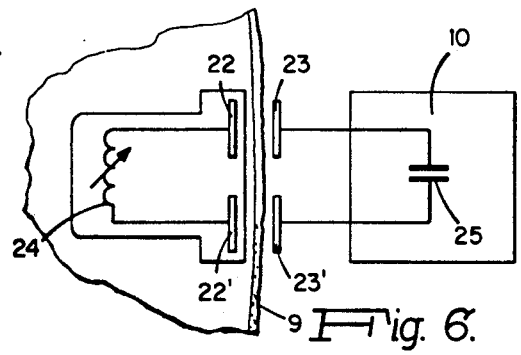
FIG. 6 illustrates schematically another means of coupling through the skin.

Referring to FIG. 6 the variable pressure sensing inductor 24 is coupled transcutaneously by area electrode pairs 22 and 22' and 23 and 23' to an external capacitor 25 which is integrated into the active external oscillator system that is contained in the external detection system 10. The frequency of oscillations of the external oscillator in 10 is determined by the L-C circuit made up of 24 and 25 and thus determines the balance condition and intracranial pressure which is read out by 10.

Figure 7:
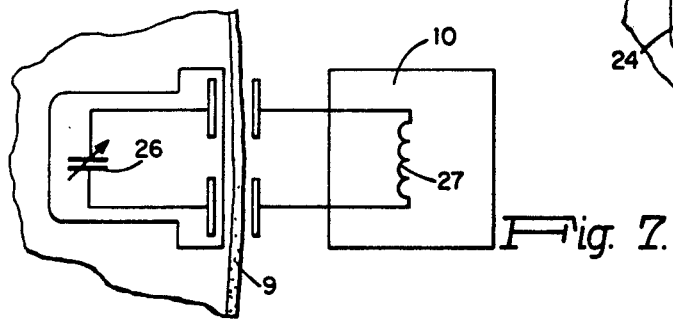
FIG. 7 illustrates yet another means of coupling through the skin.

Referring to FIG. 7, the implanted sensor contains the pressure sensitive capacitor 26, and the external active oscillator in 10 contains the complementary inductor 27.

Figure 8:
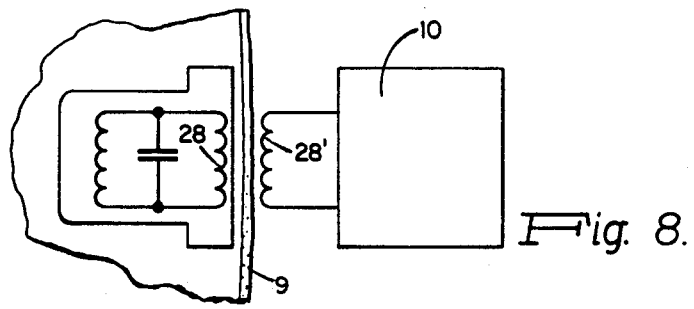
FIG. 8 is yet another coupling scheme.

Referring to FIG. 8, the transcutaneous coupling is shown to be inductive rather than capacitive. The implanted L or C may be pressure sensitive, or the implant may contain only L or only C analogously to FIG. 6 and FIG. 7. The implanted coil 28 is coupled to external coil 28', thus achieving the necessary coupling through the skin to the external oscillator in 10. Again, as in designs of FIGS. 5, 6 and 7 the frequency of the external oscillator is determined by the L-C value of the pressure sensitive tank circuit.

Other embodiments of the basic designs disclosed above can be devised for other types of pressure measurements within the body and head. To take as illustrative examples in the case of measuring intracranial pressure, the present invention can be used in conjunction with other functional devices, such as catheters, valves, shunts, flushing devices, reservoirs, filters, anti-siphon devices, and so on, to form a more diverse or multi-purpose intracranial pressure monitoring and control system. Some important illustrations are given below.

Referring to FIG. 9, the invention is shown connected to a ventricular catheter 29, which penetrates the brain 3 to the depth of the ventrical space 30 and samples the cerebrospinal fluid 31 therein through the holes 32. This device would then measure intraventricular fluid pressure. The catheter is usually made of silicone rubber and is an integral continuation of the encapsulation of the pressure sensor. Some variations in the designs of FIGS. 1 and 2 are also included in FIG. 9. A single diaphragm 7 is used and attached to a ferrite or magnetic cylinder 14 with a thinner geometry of the coil 12 and sensor body 5. The magnetic cylinder may be spring loaded with its equilibrium position on the shoulder 11. In operation the hydrostatic pressure of the ventricular cerebrospinal fluid is transmitted to the inner side of the diaphragm 7 and the opposing atmospheric pressure is transmitted through the skin to the outer side of the diaphragm, and the magnetic slug's displacement is proportional to the difference in pressures. The barometric compensation, zero checking, and other features of the sensor of FIGS. 1 and 2 are the same. Such catheterization makes measurement of pressures in other parts of the body readily possible.

Referring to FIG. 10, the pressure sensor invention is attached to a ventricular cathetor 29 [in FIG. 9] and the sampled ventricular fluid 31 is shunted past the sensor to the heart or stomach by a distal cathetor 33. A valve 34 is actuated by the lower diaphragm 7 so that as ventricular pressure rises the magnetic slug 14 and motion coupled diaphragms 7 and 7' move upward and the valve 34 increases its opening allowing more fluid to be shunted from the brain. Also shown in element 35, in series with the pressure monitor-shunt, which may be an on-off switch, reservoir, or one way flow control as usually built into systems for controlling hydroce phalus.

Referring to FIG. 11, the diagram illustrates the application of the invention as a differential pressure sensor of relative internal pressures within the body.

Cathetor 29 communicates pressure of fluid pressure in the brain to the chamber 34 to the lower side of flexible diaphragm 7 which is attached to, and actually envelopes in FIG. 11, the magnetic material slug 14. The coil 12 is embedded in the body and the spring may be a flat spring also embedded in the body, or the sensor may rely on the elasticity of the flexible diaphragm 7 itself to provide the spring constant. Another cathetor 33 is attached to the body 5 and communicates pressure from a second anatomical region, such as the heart or peritoneum, to the upper chamber 35 and the upper side of flexible diaphragm 7. In operation a difference in pressures in chambers 34 and 35 would result in a force imbalance on 7 and 14 and the consequent displacement would be detected by an external detector system. Manual pressure on the skin 9 above the implanted sensor can deflect the outside wall 36 of chamber 35 causing it to indent so as to bring magnetic slug 14 against a seat or stop (not shown). Thus, the zero-point of the differential pressure sensor can be calibrated at any time after implantation.

Figure 12:
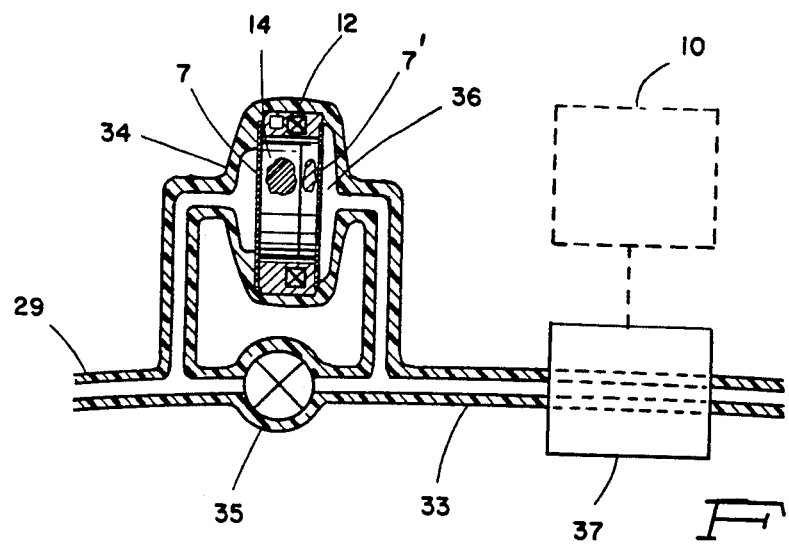
FIG. 12 illustrates a differential pressure sensor in combination with a fluid shunt valve and a fluid regulator.

Referring to FIG. 12, there is shown another configuration of the invention, used as a differential pressure sensor and combined with a fluid shunt valve and a fluid regulator or zeroing device 37. As in FIG. 11, the cathetor 29 communicates brain fluid pressure to chamber 34 and flexible diaphragm 7 as well as to the fluid shunt valve 35; and cathetors 33 and 33' communicate fluid pressure from another region, such as the heart, to the flexible diaphragm 7' and chamber 36 and carry exiting fluid away from valve 35. The difference in pressures are measured by the displacement of 14, 7 and 7' relative to coil 12 as described above. This integral system thus serves to measure and regulate flow. In addition, device 37 interposed in cathetors 33 and 33' serves to allow an external pressure to be applied on the fluid in 33 and 36' so as to zero, the dual diaphragm system 7, 7', and 14. Device 37 may be, for example, a double domed flexible rubber reservoir which enables by a digital pressure through the skin closure of passage between 33 and 33' and subsequently, be a second manual pressure, an increase in the pressure in 36. Device 37 could also be a feedback controlled valve or switch, which, upon sensing the differential pressure across 34 and 36 by the external detector 10, a controlled feedback is used to actuate a valve in 37 in such a way as to drive the differential pressure in a desired direction. This feedback process could be carried out automatically by an electro-mechanical servo system or by manual manipulation on the skin.

Figure 13:
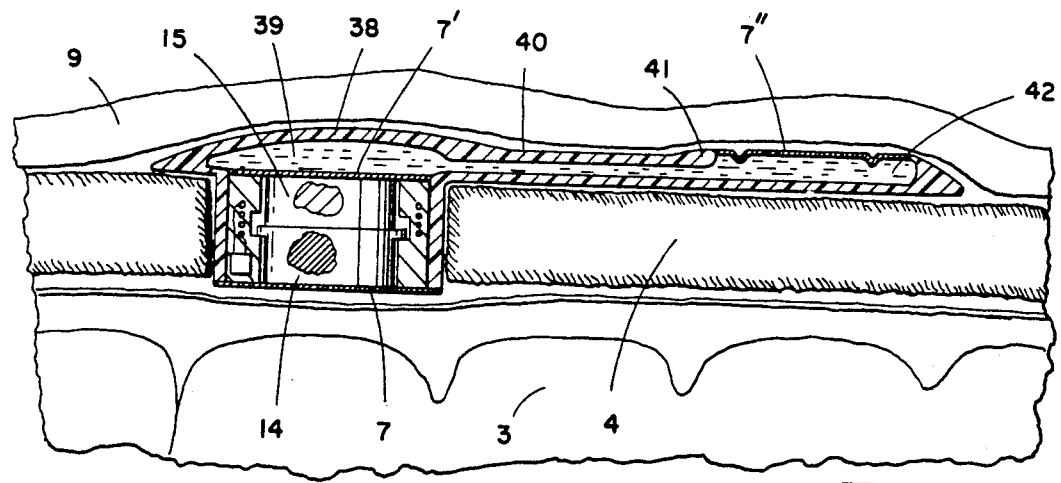
FIG. 13 illustrates a pressure sensor in which pressure is communicated to an upper diaphragm through a closed fluid system.

Referring to FIG. 13, another embodiment of the invention is illustrated for which the pressure communicated to the upper flexible diaphragm is supplied by a closed fluid system, rather than directly across the adjacent skin as in FIG. 2. In FIG. 13, a semi-rigid housing 38 covers diaphragm 7' with a space between them. The housing 38 is connected by a tube 40 to a second housing 41 which lies flat against the skull and which is covered on its upper side by a third flexible diaphragm 7''', this communicating with the skin above it and thereby with the atmospheric or any other externally applied pressure on the skin. A fluid fills the volume 39, the tube 40, and the space 42 inside 41. The system is then a triple motion-coupled diaphragm arrangement. The first two diaphragms 7 and 7' plus the magnetic piston 14 and coaxial piston 15 act the same as described above, and the differential pressure on 7 and 7' is sensed by an external detector system. The pressure applied against 7' is now transmitted to it by the fluid-filled system comprising 38, 40, 41, and 7'''. Barometric compensation again is automatic since atmospheric pressure on the skin above the third diaphragm 7''' will be transmitted through the fluid to 7'. An applied external pressure on the skin above 7''' will also be transmitted to 7'; and this could serve (a) to zero the magnetic piston 14 plus 15 and thus check the zero-point of the entire system, or (b) to supply a known and calibrated external pressure to 7' so as to balance the internal pressure on 7 and thus measure it by a pressure nulling method.

A configuration similar to that in FIG. 13 is possible where only two flexible diaphragms are used and the differential pressure implant is cathetorized to measure a remote pressure in the ventricles, as was illustrated in FIGS. 9 and 10.

Figure 14:
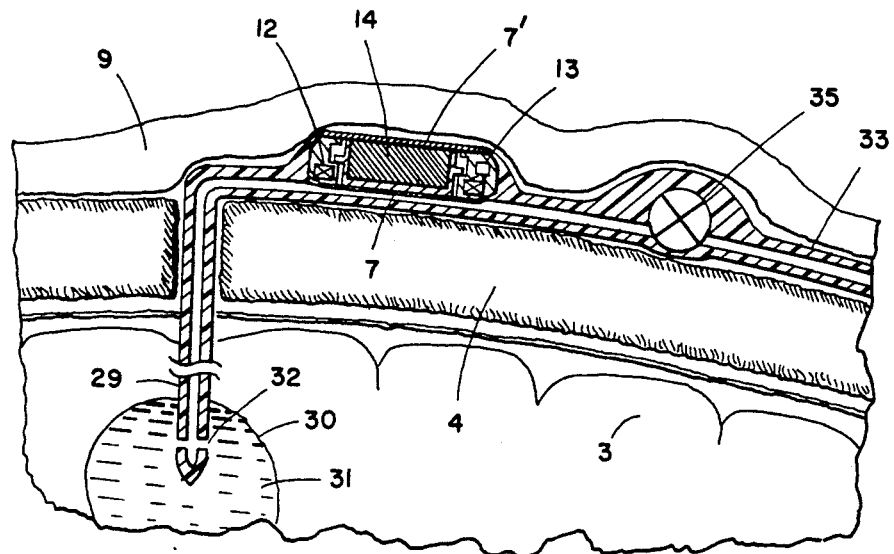
FIG. 14 illustrates another configuration similar to that shown in FIG. 10, except that the differential pressure sensor functions only as a pressure measuring device and not as a variable valve.

FIG. 14 illustrates a unified serial combination of the invention with a fluid shunt valve. This is similar to that in FIG. 10 except the differential pressure sensor acts only as a pressure measuring device and not as a variable valve too. The configuration is more compact and requires a smaller hole in the skull.

Having described in detail various embodiments of my invention, it will now be apparent to those skilled in the art that numerous modifications can be made therein without departing from the scope of the invention as defined in the following claims. For example, external manipulation of the diaphragm can be achieved by fluidly coupling a pressure source to the diaphragm by means of a fluid filled tube extending through the skin to the diaphragm.

What I claim and desire to secure by Letters Patent of the United States is:

1. A method for remotely detecting in vivo pressure, said method comprising the steps of:
   (a) implanting in a living body a differential pressure sensor comprising:
      (1) a housing having means defining an opening extending therethrough;
      (2) flexible diaphragm means extending across said housing opening and being secured with respect to said housing, said diaphragm means communicating with pressures in two separate regions external to the sensor with the pressure in one of the regions being an internal bodily pressure when the sensor is implanted in a living body;
      (3) means for defining a mechanical contact reference position of said flexible diaphragm means with respect to said housing; and,
      (4) means having a preselected, detectable parameter, the preselected, detectable parameter being detectable by detection means located outside the living body, said means having a preselected, detectable parameter being at least in part cooperatively connected to and movable with said flexible diaphragm means so that said preselected detectable parameter will change with movement of said flexible diaphragm means, such that the value of said preselected, detectable parameter changes as a known function of the displacement of said flexible diaphragm means from the reference position, said displacement being a known function of the differences in the external pressures on said flexible diaphragm means;
   (b) calibrating the implanted sensor by:
      (1) manipulating the sensor through the intact skin of the body to cause the flexible diaphragm means to assume the mechanical contact reference position;

(2) remotely detecting the value of the preselected, detectable parameter when the flexible diaphragm means is at the mechanical contact reference position;

(3) terminating the manipulation of the sensor; and, (c) thereafter remotely detecting any change in the value of the preselected, detectable parameter from the value at the mechanical contact reference position, said detecting being accomplished without any connection to the sensor which requires a break in the skin, whereby a change in said value represents the difference in pressures on the flexible diaphragm means.

2. A method for remotely detecting in vivo pressure, said method comprising the steps of:

(a) implanting in a living body a differential pressure sensor comprising:

(1) a housing having means defining an opening extending therethrough;

(2) flexible diaphragm means extending across said housing opening and being secured with respect to said housing, said flexible diaphragm means communicating with pressures in two separate regions external to the sensor with the pressure in one of the regions being an internal bodily pressure when the sensor is implanted in a living body;

(3) means for defining a mechanical contact reference position of said flexible diaphragm means with respect to said housing, said mechanical contact reference position corresponding to a known pressure relationship between the pressures in the two separate regions; and (4) means having a preselected, detectable parameter, the preselected, detectable parameter being detectable by detection means located outside the living body, said means having a preselected, detectable parameter being at least in part cooperatively connected to and movable with said flexible diaphragm means so that said preselected detectable parameter will change with movement of said flexible diaphragm means, such that the value of said preselected, detectable parameter changes as a known function of the displacement of said flexible diaphragm means from the mechanical contact reference position, said displacement being a known function of the difference in the external pressures on said flexible diaphragm means;

(b) calibrating the implanted sensor by:

(1) manipulating the sensor to cause the flexible diaphragm means to assume the mechanical contact reference position;

(2) remotely detecting the value of the preselected, detectable parameter when the flexible diaphragm means is at the mechanical contact reference position;

(3) terminating the manipulation of the sensor; and, (c) thereafter remotely detecting any change in the value of the preselected, detectable parameter from the value at the mechanical contact reference position, said detecting being accomplished without any connection to the sensor which requires a break in the skin, whereby a change in value represents the difference in pressures on the flexible diaphragm means.

3. A method for measuring an in vivo pressure, said method comprising the steps of:

(a) implanting in a living body a differential pressure sensor comprising:

(1) a housing having an opening therein;

(2) a flexible diaphragm means having a first side and a second side, said flexible diaphragm means extending across said housing opening and being secured with respect to said housing so that when the sensor is implanted in the living body, the first side of said flexible diaphragm means is in pressure communication with an internal bodily pressure to be measured and the second side of said flexible diaphragm means is in mechanical pressure communication with the interior side of a portion of skin and thereby in pressure communication across the intact skin with atmospheric pressure external to the living body on the exterior side of the portion of skin, whereby the motion of said flexible diaphragm means is responsive to the changes in the difference between said internal bodily pressure and atmospheric pressure on said exterior side of the portion of skin whereby the sensor is compensated for said atmospheric pressure;

(3) means defining a mechanical contact reference position with respect to said housing of said flexible diaphragm means, said mechanical contact reference position corresponding to a known pressure relationship between the pressures in the two separate regions;

(4) means having a preselected, detectable parameter, the preselected, detectable parameter being detectable by detection means located outside the living body, said means having a preselected, detectable parameter being at least in part cooperatively connected to and movable with said flexible diaphragm means so that said preselected detectable parameter will change with movement of said flexible diaphragm means, such that the value of said preselected, detectable parameter is detectable by detection means external to said living body, said preselected, detectable parameter changing as a known function of changes in said difference of pressures on said flexible diaphragm means from the predetermined pressure relationship at said mechanical contact reference position;

(b) calibrating the implanted sensor by:

(1) manipulating the sensor through the intact skin of the body to cause the flexible diaphragm means to assume said mechanical contact reference position;

(2) remotely detecting the value of the preselected, detectable parameter when the flexible diaphragm means is at said mechanical contact reference position;

(3) termination of the manipulation of the sensor; and, (c) thereafter remotely detecting any change in the value of the preselected, detectable parameter from the value at the mechanical contact reference position by the external detection means, said detecting being accomplished without any connection to the sensor which requires a break in the skin, whereby a change in value is related to the difference in said pressures on said flexible diaphragm means.

4. The method of claim 3 wherein said flexible diaphragm means comprises a multiplicity of pressure responsive diaphragms that are incompressibly motion coupled together, and further comprising the step of implanting said sensor in the living body so that at least one side of one of said pressure responsive diaphragms is in pressure communication with said internal bodily pressure to be measured, and at least one side of one of said pressure responsive diaphragms is in mechanical contact with said interior side of said portion of skin.

5. The method of claim 3 in which said means for defining a mechanical contact reference position comprises a mechanical stop for at least a portion of said flexible diaphragm means relative to said housing, and further comprising the step of varying said known external variable pressure until said flexible diaphragm means is driven against said mechanical stop.

6. The method of claim 3 wherein said reference position defining means includes electrode contacts that touch at a reference position relative to said housing of (i) at least a portion of said diaphragm means or (ii) a portion of said first or said second fluid communication means, said means having a preselected, detectable parameter includes circuit means within said sensor cooperative with said electrode contacts further comprising the step of forcing said contacts to touch to produce a detectable characteristic response of said circuit means.

7. The method of claim 3 further comprising the step of establishing said mechanical contact reference position so that said position corresponds to the balance of pressures in communication with said first and said second sides of said flexible diaphragm means.

8. The method of claim 7 wherein said preselected, detectable parameter is selected to provide changes in the parameter with changes in the difference in pressures on said first and said second sides of said flexible diaphragm means.

9. The method of claim 3 wherein said sensor is manipulated to establish its zero point calibration by pressing on the intact skin above the sensor so that said flexible diaphragm means assumes said mechanical contact reference position.

10. The method of claim 3 further comprising the step of precalibrating said preselected, detectable parameter as a function of the difference in pressures on said first and said second sides of said flexible diaphragm means.

11. The apparatus of claim 3 further comprising the step of precalibrating said external detection means to read the internal bodily pressure automatically by precalibrating said implanted sensor's preselected, detectable parameter as a function of the difference in pressures on said first and second sides of said flexible diaphragm means.

12. The method of claim 3 wherein said means having a preselected detectable parameter comprises electronic circuit means, said preselected detectable parameter being a characteristic response parameter of said electronic circuit means further comprising the step of detecting said preselected detectable parameter by electromagnetic coupling to an electronic apparatus means located external to said living body.

13. The method of claim 3 wherein said electronic circuit means comprises a resonant electronic circuit, and said preselected, detectable parameter being a parameter of the resonant frequency response of said resonant circuit and detecting the parameter of the resonant frequency of said resonant circuit.

14. The method of claim 3 wherein said resonant electrical circuit is a parallel resonant circuit and wherein said preselected, detectable parameter is the resonant frequency of said parallel resonant circuit and detecting the parameter of the resonant frequency of said parallel resonant circuit.

15. The method of claim 3 further comprising the step of enabling bodily fluid from an internal bodily region to communicate with one side of said flexible diaphragm means such that pressure of said bodily fluid is sensed.

16. The method of claim 3 wherein said sensor housing has an extension that forms part of a chamber on the first side of said flexible diaphragm means, and wherein a second flexible diaphragm means extends across the end of said housing opening and is fluid pressure sealed with respect to said housing so that said first and second diaphragm means and a portion of said housing form a closed volume, said closed volume being filled with a fluid to provide incompressible motion coupling of said two diaphragm means, and further comprising the step of implanting said sensor so that said second diaphragm means is in pressure communication with said internal bodily pressure to be measured.

17. A method for remotely detecting in vivo pressure, said method comprising the steps of:
a. implanting in a living body a differential pressure sensor comprising:
(1) a housing having means defining an opening extending therethrough;
(2) flexible diaphragm means extending across said housing opening and being secured with respect to said housing; said flexible diaphragm means communicating with pressures in two separate regions external to the sensor that are separated by the flexible diaphragm means with the pressure in one of the regions being an internal bodily pressure when the sensor is implanted in a living body;
(3) means for defining a reference position of said flexible diaphragm means with respect to said housing; and,
(4) means having a preselected, detectable variable parameter that is a known function of the displacement of said flexible diaphragm means from the reference position, said displacement being a known function of the differences in the external pressures on said flexible diaphragm means;
b. calibrating the implanted sensor by:
(1) manipulating the sensor through the intact skin of the body to cause the sensor to assume the reference position;
(2) remotely detecting the value of the variable parameter when the sensor is in the reference position;
(3) terminating the manipulation of the sensor;
c. thereafter remotely detecting any change in the value of the variable parameter from the value at the reference position without any connection to the sensor which requires a break in the skin, said change in value representing the differences in pressures on the flexible diaphragm means of the sensor.

18. A method for remotely detecting in vivo pressure, said method comprising the steps of:
a. implanting in a living body a differential pressure sensor comprising:
(1) a housing having means defining an opening extending therethrough;
(2) flexible diaphragm means extending across said housing opening and being secured with respect to said housing; said flexible diaphragm means communicating with pressures in two separate regions external to the sensor that are separated by the flexible diaphragm means with the pressure in one of the regions being an internal bodily pressure when the sensor is implanted in a living body;
(3) means for defining a reference position of said flexible diaphragm means with respect to said housing; and, (4) means having a preselected, detectable variable parameter that is a known function of the displacement of said flexible diaphragm means from the reference position, said displacement being a known function of the differences in the external pressures on said flexible diaphragm means;

b. calibrating the implanted sensor by:
  (1) manipulating the sensor to cause the sensor to assume the reference position;
  (2) remotely detecting the value of the variable parameter when the sensor is in the reference position;
  (3) terminating the manipulation of the sensor;

c. thereafter remotely detecting any change in the value of the variable parameter from the value at the reference position without any connection to the sensor which requires a break in the skin, said change in value representing the difference in pressures on the flexible diaphragm means of the sensor.

* * * * *

UNITED STATES PATENT AND TRADEMARK OFFICE
CERTIFICATE OF CORRECTION

PATENT NO. : 4,206,762
DATED : June 10, 1980
INVENTOR(S) : Eric R. Cosman

It is certified that error appears in the above-identified patent and that said Letters Patent are hereby corrected as shown below:

Column 3, line 16, "incorporate" should read --incorporable--

Column 7, line 34, "reactive" should read --reactance--

Column 8, line 61, "in" should read -- is --

Column 9, line 36, "36" should read -- 36 --

Column 13, line 24, "to provide changes" should read -- to provide linear changes --

Signed and Sealed this

Thirtieth Day of June 1981

[SEAL]

Attest:

RENE D. TEGTMEYER

Attesting Officer

Acting Commissioner of Patents and Trademarks